(12) United States Patent
Yang et al.

(10) Patent No.: US 9,477,640 B2
(45) Date of Patent: Oct. 25, 2016

(54) NEURAL SIGNAL PROCESSING AND/OR INTERFACE METHODS, ARCHITECTURES, APPARATUSES, AND DEVICES

(71) Applicant: National University of Singapore, Singapore (SG)

(72) Inventors: Zhi Yang, Singapore (SG); Jian Xu, Singapore (SG)

(73) Assignee: NATIONAL UNIVERSITY OF SINGAPORE, Singapore (SG)

( * ) Notice: Subject to any disclaimer, the term of this patent is extended or adjusted under 35 U.S.C. 154(b) by 438 days.

(21) Appl. No.: 13/943,759

(22) Filed: Jul. 16, 2013

(65) Prior Publication Data

US 2014/0025715 A1   Jan. 23, 2014

Related U.S. Application Data

(60) Provisional application No. 61/671,824, filed on Jul. 16, 2012.

(51) Int. Cl.
| | |
|---|---|
| *G06F 17/10* | (2006.01) |
| *G06N 3/04* | (2006.01) |
| *G06N 3/063* | (2006.01) |
| *A61B 5/04* | (2006.01) |
| *A61B 5/00* | (2006.01) |

(52) U.S. Cl.
CPC ............. *G06F 17/10* (2013.01); *G06N 3/049* (2013.01); *G06N 3/063* (2013.01); *A61B 5/04001* (2013.01); *A61B 5/72* (2013.01)

(58) Field of Classification Search
CPC ...................................................... G06F 17/10
See application file for complete search history.

(56) References Cited

U.S. PATENT DOCUMENTS

| | | | | |
|---|---|---|---|---|
| 5,162,723 A | * | 11/1992 | Marzalek | G01R 23/16 324/121 R |
| 2013/0325774 A1 | * | 12/2013 | Sinyavskiy | G06N 3/049 706/23 |

OTHER PUBLICATIONS

Jang et al., "A new EC-PC threshold estimation method for in vivo neural spike detection", Jul. 13, 2012, pp. 1-16.*
Aziz, J.N. Y., Abdelhalim, K., Shulyzki, R., Genov R., Bardakjian, B.L., & Derchansky, M., et al. 256-Channel Neural Recording and Delta Compression Microsystem With 3D Electrodes. Solid-State Circuits, IEEE Journal of. Mar. 2009;44(3):995-1005.

(Continued)

*Primary Examiner* — Chuong D Ngo
(74) *Attorney, Agent, or Firm* — Ming Chow; Sinorica, LLC

(57) ABSTRACT

Processing a neural signal sequence occurs in accordance with a neural signal spiking model that includes an exponential component (EC) and a polynomial component (PC). The exponential component is correlated with the presence of signal sequence noise, and the polynomial component is correlated with the presence of detectable signal sequence spikes distinguishable from the noise. A neural interface includes a frequency shaping amplifier (FSA) configured for receiving input signals; an amplifier gain stage and an analog-to-digital conversion (ADC) stage; a Hilbert transformer configured for performing a Hilbert transform upon neural signal data received from the ADC stage; a linear regression engine configured for estimating EC parameters and PC parameters corresponding to Hilbert transformed neural signal data; and a neural spike probability estimator configured for generating a neural spike probability map based upon the EC parameters and the PC parameters.

24 Claims, 16 Drawing Sheets

(56) References Cited

OTHER PUBLICATIONS

Lewicki, M. S.. A review of methods for spike sorting: the detection and classification of neural action potentials. Network: Computation in Neural Systems. 1998;9:53-78.

Kaneko, H., Tamura, H., & Suzuki, S. S.. Tracking spike-amplitude changes to improve the quality of multineuronal data analysis. IEEE Trans Biomedical Engineering. Feb. 2007;54(2):262-272.

Cunningham, J. P., Yu, B. M., Shenoy, K. V., & Sahani, M.. Inferring neural firing rates from spike trains using Gaussian processes. Advances in NIPS. 2008;20.

Valerie, V. & Richard, C.. Accurately estimating neuronal correlation requires a new spike-sorting paradigm. PNAS. May 2012;109(19):7230-7235.

Harrison, R. R.. The Design of Integrated Circuits to Observe Brain Activity. Proceedings of the IEEE. Jul. 2008;96 (7)1203-1216.

Chae, M., Liu, W., Yang, Z., Chen, T., Kim, J., Sivaprakasam, M. & Yuce, M.. A 128-channel 6mW wireless neural recording IC with on-the-fly spike sorting and UWB tansmitter. IEEE ISSCC Dig Tech Papers. Feb. 2008;7(6):146-147.

Karkare, V., Gibson, S., Markovic, D.. A 130uW, 64-Channel Neural Spike-Sorting DSP Chip. Solid-State Circuits, IEEE Journal of. May 2011;46(5):1214-1222.

Linderman, M. D., Santhanam, G., Kemere, C. T., Gilja, V., O'Driscoll, S., Yu, B. M., et al. Signal Processing Challenges for Neural Prostheses. Signal Processing Magazine, IEEE. 2008;25(1):18-28.

Riehle, A., Grun, S., Diesmann, M., & Ad, A.. Spike Synchronization and Rate Modulation Differentially Involved in Motor Cortical Function. Science. 1997;1997.

Quian Quiroga, R., Nadasdy, Z., & Ben-Shaul, Y. Unsupervised spike detection and sorting with wavelets and superparamagnetic clustering. Neural Computation. Aug. 2004;16(8):1661-1687.

Vollgraf, R. & Obermayer, K.. Improved optimal linear filters for the discrimination of multichannel waveform templates for spike-sorting applications. IEEE Signal Proc Let. Mar. 2006;13(3):121-124.

Dominguez-Morales, M., Jimenez-Fernandez, A., Cerezuela-Escudero, E., Paz-Vicente, R., Linares-Barranco, A., & Jimenez G.. On the Designing of Spikes Band-Pass Filters for FPGA. 2011;6792:389-396.

Olsson, R. & Wise, K. D. A three-dimensional neural recording microsystem with implantable data compression circuitry. IEEE ISSCC 2005 Dig Tech Papers. 2005 558-559;(30).

Mohseni, P. & Najafi, K. A Battery-Powered 8-Channel Wireless FM IC for Biopotential Recording Applications. IEEE ISSCC 2005 Dig Tech Papers. Feb. 2005;30(5):560-561.

Harrison, R., Watkins, P., Kier, R., Lovejoy, R., Black, D., Normann, R., et al. A Low-Power Integrated Circuit for a Wireless 100-Electrode Neural Recording System. IEEE ISSCC 2006 Dig Tech Papers. Feb. 2006;30(2):2258-2267.

Aziz, J., Genov, R., Derchansky, M., Bardakjian, B., & Carlen, P.. 256-Channel Neural Recording Microsystem with On-Chip 3D Electrodes. IEEE ISSCC 2007 Dig Tech Papers. Feb. 2007;8(5):160-161.

Denison, T., Consoer, K, Kelly, A., Hachenburg, A., & Santa, W.. A 2.2 W 94nV=pHz, Chopper-Stabilized Instrumentation Amplifier for EEG Detection in Chronic Implants. IEEE ISSCC 2007 Dig Tech Papers. Feb. 2007;8(6).

Sarpeshkar, R., Wattanapanitch, W., Arfin, S. K., Rapoport, B. I. , Mandal, S., Baker, M. W., et al. A Low-Power Circuits for Brain-Machine Interfaces. IEEE Trans Biomed Circuits Syst. Sep. 2008;2(3):173-183.

Chae, M., Liu, W., Yang, Z., Chen, T., Kim, J., Sivaprakasam, M., et al. A 128-Channel 6mW Wireless Neural Recording IC with On-the-Fly Spike Sorting and UWB Tansmitter. IEEE ISSCC Dig Tech Papers. Feb. 2008;7(6):146-147.

Mollazadeh, M., Murari, K. Cauwenberghs, G., & Thakor, N.. Micropower CMOS Integrated Low-Noise Amplification, Filtering, and Digitization of Multimodal Neuropotentials. IEEE Trans Biomed Circuits Syst.Feb. 2009;3(1):1-10.

Gosselin, B., Ayoub, A., Roy, J., Sawan, M., Lepore, F., Chaudhuri, A., et al. A Mixed-Signal Multichip Neural Recording Interface With Bandwidth Reduction. IEEE Trans Biomed Circuits Syst. Jun. 2009;3(3):129-141.

Lee, S., Lee, H., Kiani, M., Jow, U., & Ghovanloo, M.. An Inductively Powered Scalable 32-Channel Wireless Neural Recording System-on-a-Chip for Neuroscience Applications. IEEE ISSCC 2010 Dig Tech Papers. Feb. 2010;6(4):120-121.

Xiao, Z., Tang, C., Dougherty, C., & Bashirullah, R.. A 20uW Neural Recording Tag with Supply-Current-Modulated AFE in 0.13m CMOS. IEEE ISSCC 2010 Dig Tech Papers. Feb. 2010;6(5):122-123.

Shahrokhi, F., Abdelhalim, K., Serletis, S., Carlen, P. L., & Genov, R.. The 128-Channel Fully Differential Digital Integrated Neural Recording and Stimulation Interface. IEEE Trans Biomed Circuits Syst. Jun. 2010;4(3):149-161.

Muller, R., Gambini, S., & Rabaey, J. A 0.013mm2 5 W DC-coupled neural signal acquistion IC with 0.5V supply. IEEE ISSCC Dig Tech Papers. Feb. 2011;17(2):302-303.

Yang, Z., Zhao, Q., Keefer, E., & Liu, W. Noise Characterization, Modeling, and Reduction for in Vivo Neural Recording. Advances in Neural Information Processing Systems 22. 2010;p. 2160-2168.

\* cited by examiner

Timing Diagram

NEURAL SIGNAL PROCESSING AND/OR INTERFACE METHODS, ARCHITECTURES, APPARATUSES, AND DEVICES

TECHNICAL FIELD

The present disclosure relates generally to neural signal processing and neural signal interfaces. More particularly, an embodiment of the present disclosure is directed to aspects of a neural signal processing system in which a signal or data sequence (e.g., captured or modeled/simulated neural signals) can be processed in accordance with a neural signal spiking model that includes an exponential component and a polynomial component. An embodiment of the present disclosure is also directed to aspects of a neural signal interface architecture.

BACKGROUND

In neural signal processing, the detection or identification of individual neural spikes within sequences of neural signals is important for facilitating or enabling neural signal decoding or interpretation. Unfortunately, neural signals exhibit unpredictable nonlinear behavior, including non-stationary noise, amplitude/waveform fluctuations, and firing state/firing rate transitions. As a result, the accurate and reliable identification of neural spikes is difficult.

In spite of several decades of research, no sufficiently robust neural signal processing technique currently exists that can accurately and reliably identify individual neural spikes within a wide variety of actual or "real world" neural signal sequences about which prior knowledge does not exist, or with respect to which a priori assumptions cannot be made. Furthermore, to date no neural signal processing architecture exists that can readily be scaled for processing neural signal data corresponding to small, moderate, or substantial populations of neurons (e.g., hundreds, thousands, or millions of neurons, respectively).

A need exists for a neural signal processing architecture that overcomes such problems.

SUMMARY

In accordance with a first aspect of the present disclosure, a process for processing or analyzing neural signals includes (a) providing a signal sequence that includes a plurality of signal values; and (b) processing the signal sequence in accordance with a neural signal spiking model that includes an exponential component and a polynomial component, wherein the exponential component is correlated with the presence of noise within the signal sequence and the polynomial component is correlated with the presence of detectable spikes within the signal sequence distinguishable from the noise.

The exponential component corresponds to background noise within the signal sequence that satisfies the Central Limit Theorem; and the polynomial component corresponds to the occurrence of spikes within the signal sequence that violate Lyapunov's condition. The magnitude of the polynomial component relative to the magnitude of the exponential component increases in response to each of increased spike magnitude and increased spike occurrence frequency within the signal sequence.

The exponential component is mathematically correlated with an equation of the form $$e^{-\lambda_1 Z}$$

and the polynomial component is mathematically correlated with an equation of the form $$Z^{-\lambda_2}.$$

In multiple embodiments, $\lambda_1$ approximately equals 0.5, and $\lambda_2$ approximately equals 2.5.

Processing the signal sequence can include determining an instantaneous power value Z, wherein the neural signal spiking model corresponds to a probability density function f(Z) for which the presence of signal values within the signal sequence corresponding to noise gives rise to f(Z) behaving in accordance with the exponential component and the presence of signal values within the signal sequence corresponding to neural spikes gives rise to f(Z) behaving in accordance with the polynomial component.

Processing the signal sequence can additionally include performing a Hilbert transform upon the provided signal sequence. Processing the signal sequence can further include determining a spike detection threshold corresponding to a mathematical crossover point between the exponential component and the polynomial component; and determining a probability that a signal value within the signal sequence corresponds to one of noise and a spike.

The process can also include generating a spiking probability map corresponding to the signal sequence, the spiking probability map indicating which signal values within the signal sequence correspond to neural spikes; and outputting a sequence of spike indicators based upon the spiking probability map. A data rate corresponding to the sequence of spike indicators can be approximately 1000 times less than a raw data rate corresponding to recorded neural signals.

In accordance with an aspect of the present disclosure, a neural interface includes a frequency shaping amplifier (FSA) configured for receiving input signals corresponding to neuroelectric activity; and an amplifier gain stage coupled to receive and amplify signals output by the FSA. Such a neural interface inherently rejects electrode offset voltage $V_{off}$ by way of the FSA, and the neural interface excludes a DC high pass filter configured for filtering electrical signals that are input to the neural interface and which correspond to neuroelectric activity.

The neural interface also includes at least some of (a) an analog-to-digital conversion (ADC) stage coupled to the amplifier gain stage, the ADC stage configured for converting amplified FSA output signals to digital signals; (b) a Hilbert transformer coupled to the ADC stage, the Hilbert transformer configured for performing a Hilbert transform upon neural signal data received from the ADC stage; (c) a linear regression engine coupled to the Hilbert transformer, the linear regression engine configured for estimating exponential component (EC) parameters and polynomial component (PC) parameters corresponding to Hilbert transformed neural signal data; and (d) a neural spike probability estimator configured for generating a neural spike probability map based upon the EC parameters and the PC parameters.

In accordance with a further aspect of the present disclosure, a neural signal processor includes a Hilbert transformer having a set of inputs at which neural signal data is receivable, the Hilbert transformer configured for performing a Hilbert transform upon received neural signal data; a linear regression engine coupled to the Hilbert transformer, the linear regression engine configured for estimating exponential component (EC) parameters and polynomial component (EC) parameters corresponding to Hilbert transformed neural signal data; and a neural spike probability estimator configured for generating a neural spike probability map based upon the EC parameters and PC parameters.

DETAILED DESCRIPTION

Figure 1:
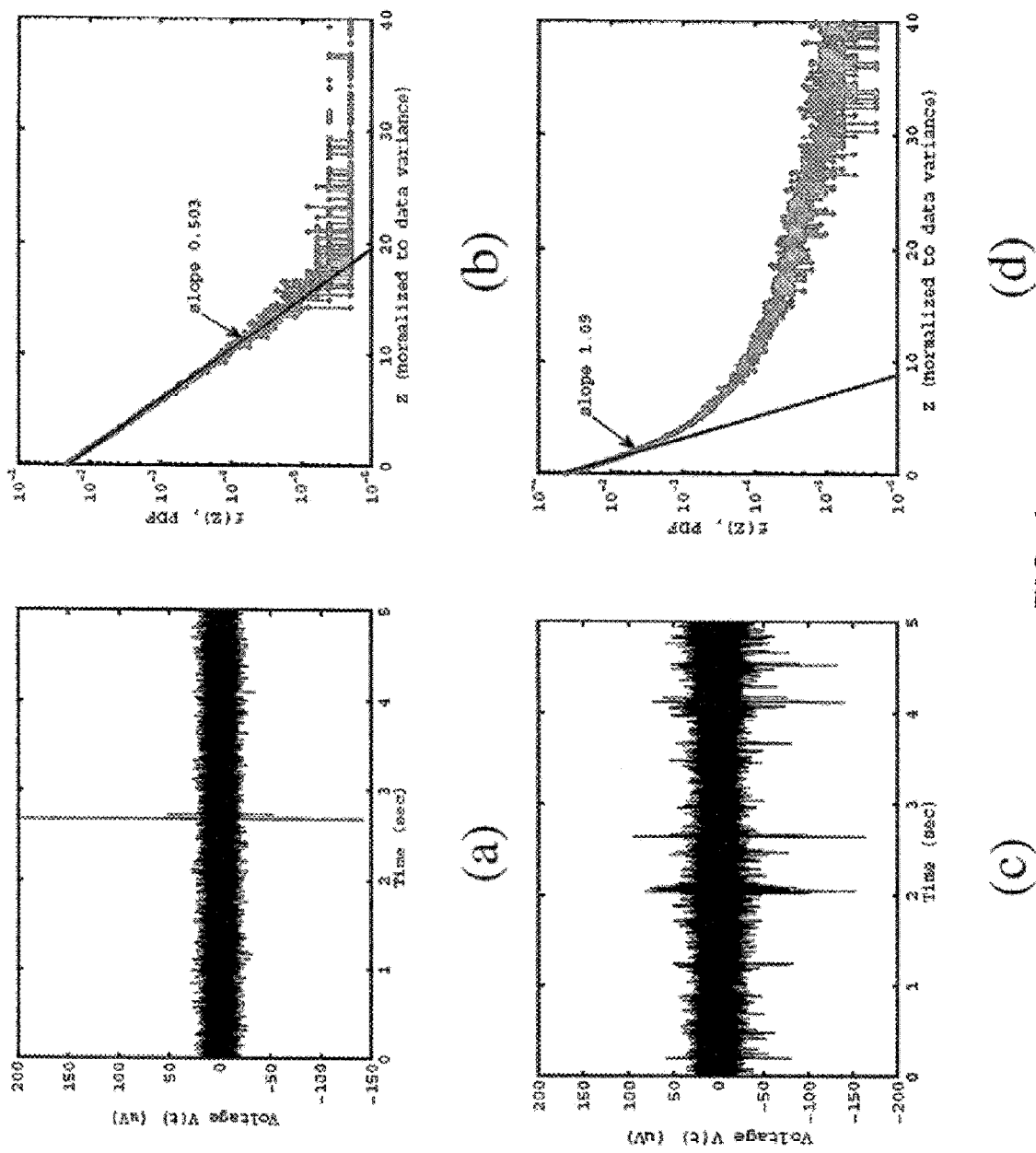
FIG. 1A is an illustration of a neural signal or data sequence having relatively few visually detectable spikes.
FIG. 1B is an illustration of a cumulative probability distribution function f(Z) corresponding to the neural data sequence of FIG. 1A, fitted in accordance with an exponential function over 4 orders.
FIG. 1C is an illustration of a neural signal or data sequence having relatively more visually detectable spikes than the neural data of FIG. 1A.
FIG. 1D is an illustration of f(Z) corresponding to the neural data sequence of FIG. 1C, illustrating the deviation of f(Z) away from exponential behavior as a result of the presence of neural spikes within the neural data sequence.

In the present disclosure, the depiction of a given element or consideration or use of a particular element number in a particular FIG. or a reference thereto in corresponding descriptive material can encompass the same, an equivalent, or an analogous element or element number identified in another FIG. or descriptive material associated therewith. Unless explicitly stated otherwise, the recitation of particular numerical values or value ranges in the present disclosure is taken to be a recitation of particular approximate numerical values or approximate value ranges (e.g., within 0.5%-10%, or 1%-5%, of specified numerical values or ranges). Additionally, the use of "/" in the present disclosure implies "and/or" unless specifically indicated otherwise.

As used herein, the term "set" corresponds to or is defined as a non-empty finite organization of elements that mathematically exhibits a cardinality of at least 1 (i.e., a set as defined herein can correspond to a singlet or single element set, or a multiple element set), in accordance with known mathematical definitions (for instance, in a manner corresponding to that described in *An Introduction to Mathematical Reasoning: Numbers, Sets, and Functions*, "Chapter 11: Properties of Finite Sets" (e.g., as indicated on p. 140), by Peter J. Eccles, Cambridge University Press (1998)). In general, an element of a set can include or be a system, an apparatus, a device, a structure, a structural feature, an object, a process, a physical parameter, or a value depending upon the type of set under consideration.

Embodiments of the present disclosure are directed to aspects of architectures, systems, apparatuses, devices, methods, and/or procedures for facilitating or effectuating one or each of (a) capturing or recording neural signals; (b) processing neural signals, and (c) transferring, communicating, or exchanging signals associated with one or more (i) neural populations and/or (ii) systems, apparatuses, devices, circuits, or circuit elements/structures. The terms "neural signal" and "neural signals" as used herein include signals (e.g., electrical and/or magnetic signals) correlated with, corresponding to, or representing the generation of action potentials by one or more sets of neurons (i.e., the terms "neural signal" and "neural signals" encompass neural signal correlates, such as electrical signals that can be detected as a result of neuroelectric activity within one or more neural populations).

Depending upon embodiment details and/or a neural signal interface or neural signal processing situation or environment under consideration, the terms "neuron," "neurons," and "neural population" can refer to one or more sets of (a) biological neurons; (b) artificial or synthetic neurons (e.g., nanostructure based synaptic devices such as carbon nanotube synthetic synapse circuits); and/or (c) virtual neurons that correspond to or exist in the context of a behavioral/computational model or numerical simulation. Biological neurons can exist in vivo (e.g., as a number of target neural populations within a subject's central or peripheral nervous system) or in vitro. Furthermore, biological neurons or synthetic neurons can exist as portions of a manufacturable/manufactured device or circuit (e.g., a hybrid biological—nonbiological circuit or chip), which is configured for operation internal or external to a biological organism (e.g., a mammalian body).

Aspects of a neural spiking model are described in detail in "A new EC-PC threshold estimation method for in vivo neural spike detection," Yang Z et al., J Neural Eng., 2012 August; 9(4):046017, which is incorporated herein by reference in its entirety. Aspects of a an EC-PC based integrated circuit for neural spike detection is described in detail in "A Multichannel Integrated Circuit for Neural Spike Detection Based on EC-PC Threshold Estimation," Yang Zhi and Wu Tong, Paper ThB13.9, 35$^{th}$ *Annual IEEE EMBS Conference*, Jul. 3-7, 2013, Osaka, Japan, which is also incorporated herein by reference in its entirety. Particular aspects of non-limiting representative embodiments in accordance with the present disclosure are provided hereafter for purpose of illustration in order to aid understanding.
Aspects of Representative Neural Signal Processing Models/Methodologies In accordance with an aspect of the present disclosure, a neural signal spiking model is based upon, correlated with, or includes (a) an exponential term corresponding to noise (e.g., neural noise); and (b) a polynomial or power law term corresponding to neural spiking/action potential generation that is distinguishable or distinct from noise. In accordance with the neural spiking model, a signal or data sequence, series, or pattern (e.g., sample or test signals, which can include actual/recorded neural signals; simulated/modeled neural signals; or unknown signals, which can include or exclude such neural signals) can be input, processed, decomposed, and/or analyzed in accordance with the model by way of (a) exponential component (EC) corresponding to or indicative or representative of noise, and (b) a polynomial component (PC) corresponding to or indicative or representative of neural spiking/action potential activity.

For a provided or input signal sequence that includes a plurality of signal values (e.g., a captured, recorded, or simulated neural signal or data sequence), signal values corresponding to noise are considered to conform to the conditions of the Central Limit Theorem. Consequently, a neural signal or data sequence that primarily includes noise, and which includes few neural spikes, can be expected to exhibit Gaussian or substantially Gaussian type behavior.

Within a provided or input signal sequence, signal values corresponding to neural spiking are considered to violate the Lyapunov condition. Consequently, a neural signal or data sequence that includes relatively more neural spikes than a neural signal or data sequence that primarily includes noise can be expected to deviate further from Gaussian or substantially Gaussian type behavior as the neural spike content within the signal sequence increases.

In accordance with embodiments of the present disclosure, a strong analytic signal $V_{st}$ can be defined based upon a real valued signal sequence (e.g., a neural signal or data sequence) and its Hilbert transform, as detailed in Appendices A and B. Furthermore, an instantaneous power Z can be defined corresponding to $V_{st}$, which can be normalized with respect to signal value variance within the signal sequence. Additionally, a corresponding probability density function f(Z) can be defined, as detailed in Appendices A and B.

FIG. 1A is an illustration of a neural signal or data sequence having relatively few visually detectable spikes, which can be taken to mostly include neural noise. FIG. 1B is an illustration of f(Z) corresponding to the neural data sequence of FIG. 1A, fitted in accordance with an exponential function over 4 orders. FIG. 1C is an illustration of a neural signal or data sequence having relatively more visually detectable spikes than the neural data of FIG. 1A. FIG. 1D is an illustration of f(Z) corresponding to the neural data sequence of FIG. 1C, clearly illustrating the deviation of f(Z) away from exponential behavior due to the presence of neural spikes within the neural data sequence.

In accordance with various embodiments of the present disclosure, noise that conforms to the conditions of the Central Limit Theorem gives rise to a probability density function f(Z) exhibiting exponential behavior or having an exponential component (EC), e.g., $$f(Z) \alpha e^{-\lambda_1 Z} \qquad (1)$$

Furthermore, neural spikes that violate the Lyapunov condition give rise to the probability density function f(Z) exhibiting polynomial behavior or having a polynomial component (PC), e.g., $$f(Z) \alpha Z^{-\lambda_2} \qquad (2)$$

In various situations, $\lambda_1$ approximately equals 0.5, and $\lambda_2$ approximately equals 2.5.

Embodiments in accordance with the present disclosure can process or analyze signal or data values in a manner based upon or correlated with determining an EC-PC crossing point relative to which signal values can be categorized as noise or neural spikes. Additionally, embodiments in accordance with the present disclosure can determine a probability that a given signal or data value with an instantaneous energy of $Z_o$ corresponds to noise or a neural spike. Embodiments in accordance with the present disclosure can also generate or determine a spiking probability map that indicates which signal or data values within a signal or data sequence probabilistically correspond to neural spikes rather than noise. Furthermore, embodiments in accordance with the present disclosure can estimate or determine for any given signal or data sequence an appropriate, near-optimal, or essentially-optimal threshold level, value, or range (e.g., an EC-PC crossing threshold) relative to which provided, acquired, or input signal or data values can be compared in view of determining whether a given signal or data value under consideration corresponds to noise or a neural spike. Such threshold determination can occur on an adaptive basis over time, for instance, relative to input signal or data sequences that differ or change across time (e.g., in a manner associated with the current or recent physiologic state or health of a neural population that serves as the source of the signal or data sequence).

Figure 2A:
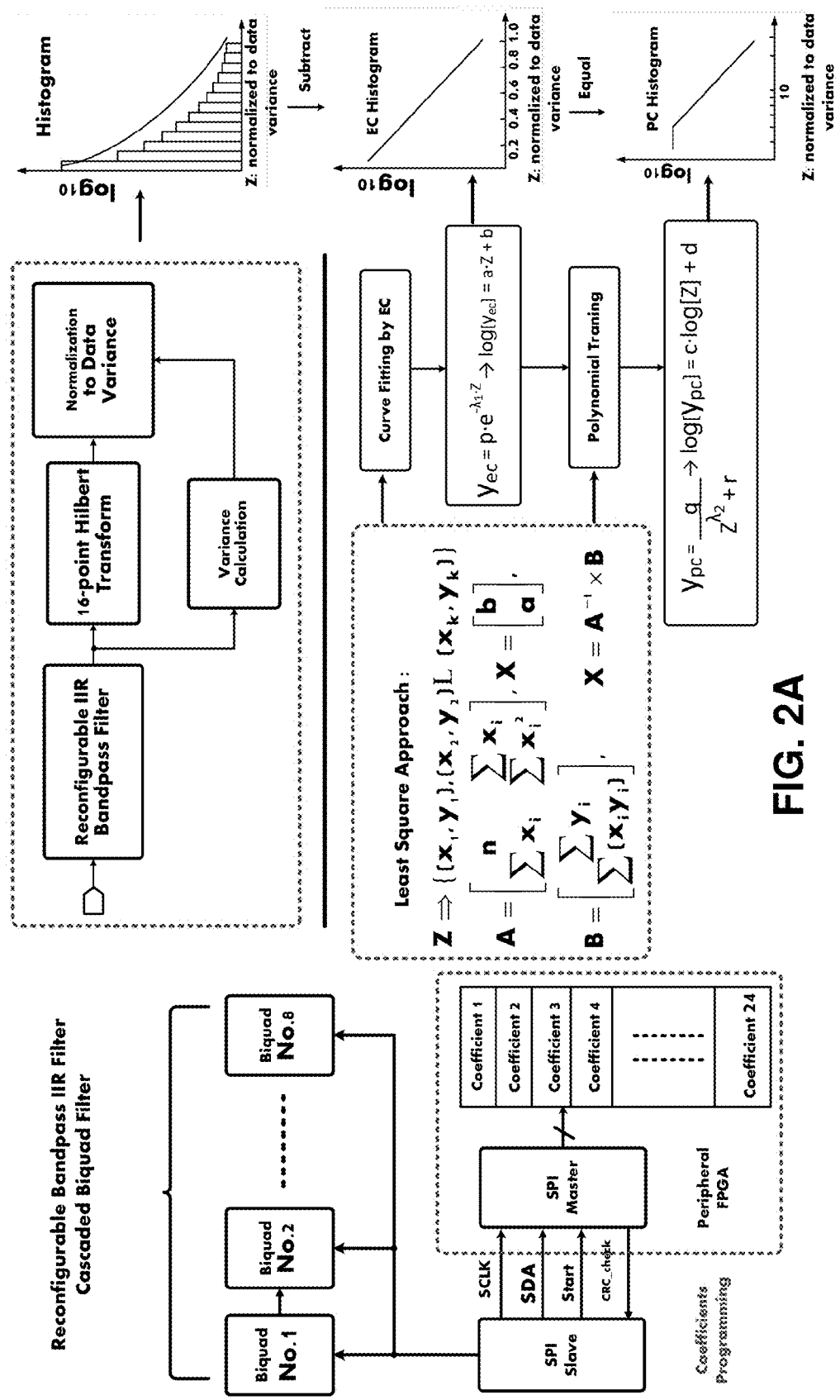
FIGS. 2A-2B illustrate a representative integrated circuit implementation of a neural signal processing system or device in accordance with an embodiment of the present disclosure.
Figure 2B:
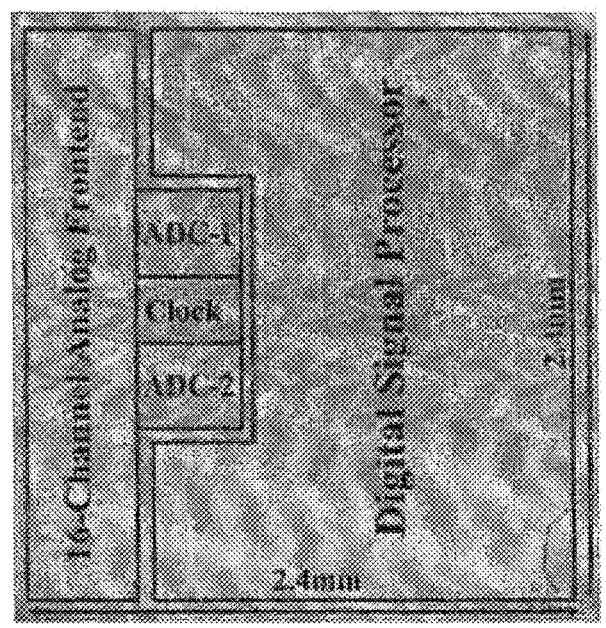

Neural signal processing in accordance with embodiments of the present disclosure can be applied to neural signal detection, feature extraction, decoding, and/or other applications. Depending upon embodiment details, neural signal processing can occur based upon program instructions (e.g., software, which is stored in a memory or computer readable medium, and which can be executed by a set of processing units), a state machine, and/or one or more types of hardware. For instance, FIGS. 2A-2B illustrate aspects of an integrated circuit implementation of a system or device configured for processing input signal sequences in accordance with an embodiment of the present disclosure.

In some embodiments, detected, captured, recorded, or generated neural signals can be provided or input to a neural signal spiking model (e.g., on a pre-recorded, delayed, or near-real-time basis), and processed in one or more manners. In a number of embodiments, the detection, capture, or recording of such neural signals can occur by way of a neural interface architecture in accordance with an embodiment of the present disclosure, as further detailed hereafter.

Aspects of Representative Neural Interface Architectures

In accordance with another aspect of the present disclosure, a neural interface architecture provides high, scalable recording density; enhanced tolerance to low frequency artifacts; reduced neural interface degeneration (e.g., corresponding to an electrode interface); and reduced requirements associated with system dynamic range. The neural interface architecture includes a frequency dependent gain stage configured for inherently rejecting DC offset and attenuating large magnitude low frequency interference. The neural interface architecture can include frequency compensation elements (e.g., digital signal processing elements) configured for restoring or reconstructing neural signals that are detected or "seen" by an electrode. Compared to existing neural interfaces, a neural interface architecture, system, or device in accordance with an embodiment of the present disclosure can result in increased amplifier input impedance (>15 times); increased dynamic range (>20 dB); and improved tolerance to artifacts and 60 Hz noise.

Figure 3A:
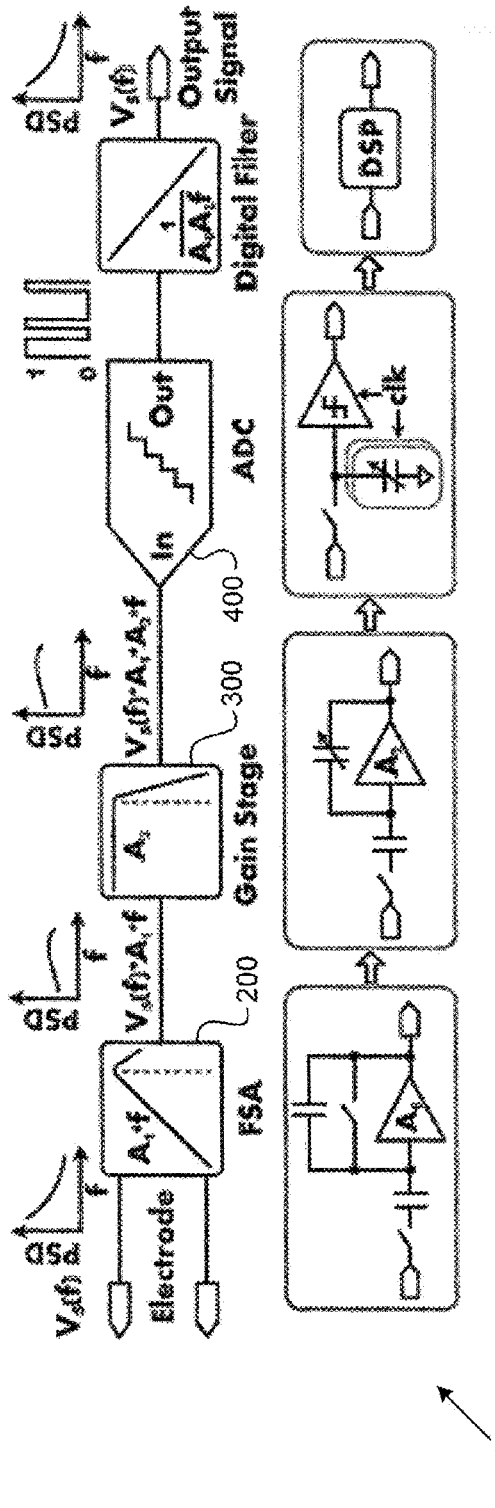
FIG. 3A is a schematic illustration of a neural interface architecture in accordance with the present disclosure.

FIG. 3A is a block diagram of a neural interface architecture 100 in accordance with an embodiment of the present disclosure. In an embodiment, the architecture 100 includes a front end having a frequency shaping amplifier (FSA) 200, which is configured for receiving signals correlated with or corresponding to neural signals. More particularly, the FSA 200 includes a set of inputs couplable or coupled to a number of electrodes that are configured for detecting or receiving electrical signals correlated with or corresponding to neuroelectric activity (e.g., action potential generation) within one or more target neural populations (e.g., a set of central nervous system neural populations, such as cortical and/or subcortical neural populations).

Figure 3B:
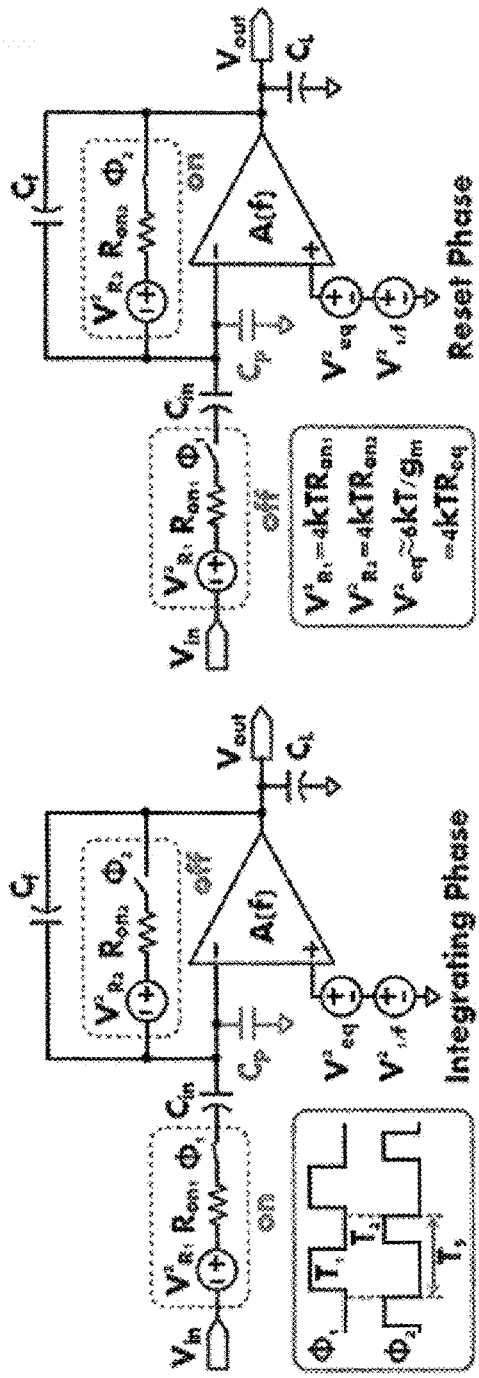
FIG. 3B is a schematic illustration of a representative embodiment of a frequency shaping amplifier (FSA) in accordance with the present disclosure.

FIG. 3B is a schematic illustration of a representative embodiment of an FSA 200 in accordance with the present disclosure. As a result of the inclusion of an FSA 200 in a neural interface architecture 100, electrode offset voltage $V_{off}$ is inherently rejected. Consequently, the neural interface architecture 100 can omit or exclude a DC high pass input signal filter, thereby simplifying neural interface design and reducing cost.

The neural interface architecture 100 further includes a gain or amplification stage 300 configured for receiving and amplifying FSA output; and an analog-to-digital conversion (ADC) stage 400, which can be configured for multiplexing amplification stage outputs and generating digital signals corresponding thereto. The neural interface architecture 100 can be coupled to or include a number of processing modules, units, circuits, or elements, such as a digital signal processing (DSP) module configured for receiving ADC stage outputs and reconstructing and/or processing neural signals detected or "seen" by a set of electrodes or other signal sources coupled to corresponding FSA inputs, for instance, to recognize/identify and communicate or process signals corresponding to neural spikes.

Further Aspects of Representative Neural Signal Recording and Processing Architectures In view of the foregoing, a neural interface architecture 100 in accordance with an embodiment of the present disclosure can be based upon or include a frequency shaping (FS) or FSA-based neural signal recording architecture, which is coupled or couplable to an EC-PC neural signal processing/discrimination architecture. Depending upon embodiment details, one or each of an FS neural signal recording architecture and an EC-PC neural signal processing architecture can be implemented by way of a single chip or a small number of chips (e.g., an Applications Specific Integrated Circuit (ASIC) or a Field Programmable Gate Array (FPGA)). In several embodiments, an FS neural signal recording architecture and an EC-PC neural signal processing architecture can reside on a single circuit board, which can be configured for wire-based or wireless communication of neural spike indicators to another (e.g., remote) system or device (e.g., a computing device such as a laptop or desktop computer). Further aspects of a representative FS neural recording architecture and a representative EC-PC neural signal processing architecture are described in detail hereafter.

Figure 4:
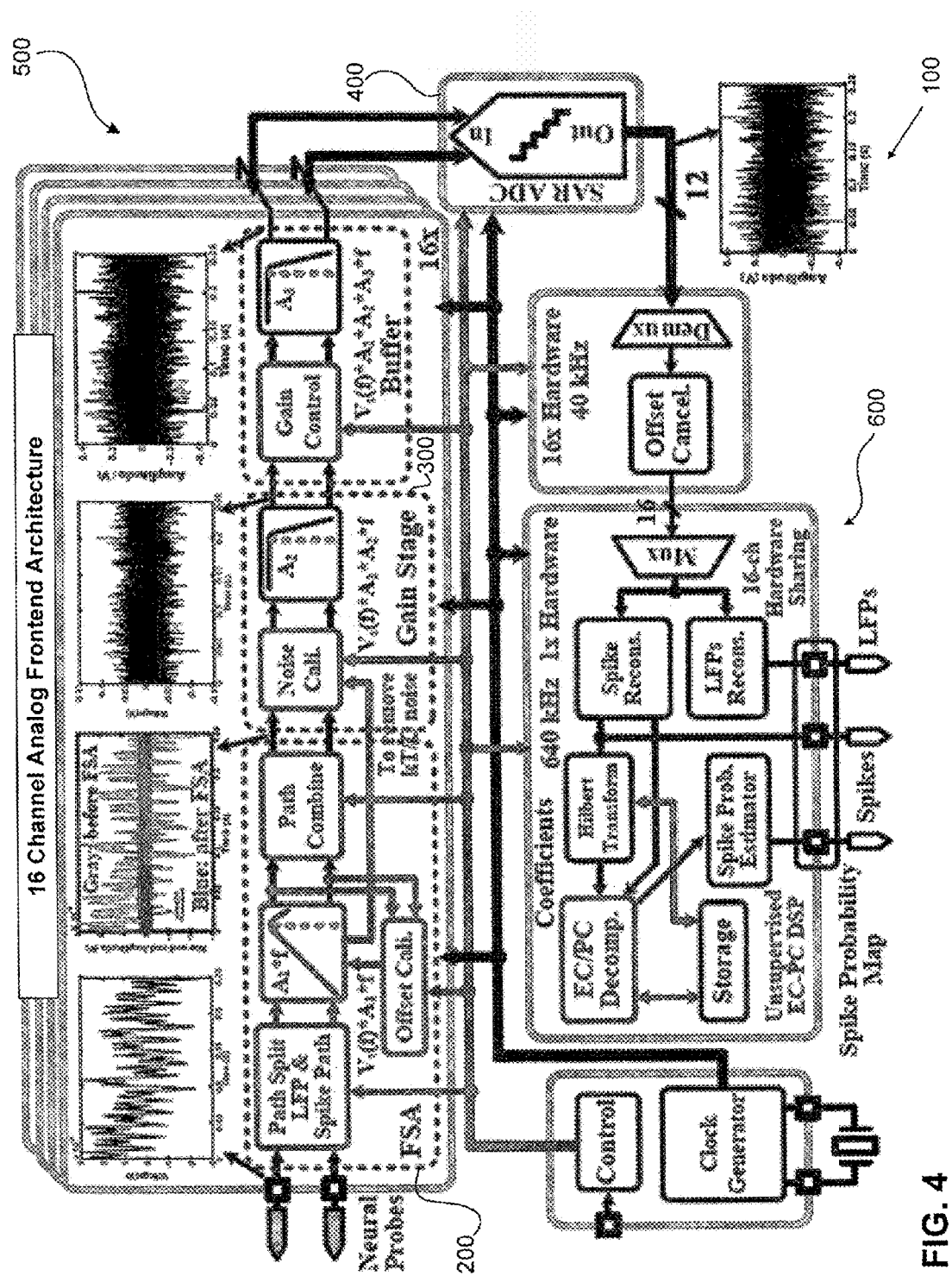
FIG. 4 is a schematic illustration of a representative neural interface architecture that includes an FS neural recording architecture and an EC-PC neural processing architecture in accordance with an embodiment of the present disclosure.

FIG. 4 is a schematic illustration of a representative neural interface architecture 100 that includes an FS neural recording architecture 500 and an EC-PC neural processing architecture 600 in accordance with an embodiment of the present disclosure. The FS neural recording architecture 500 is configured to receive neural signals (e.g., in vivo neural signals), and includes an FSA 200 that is configured to receive neural signals as inputs (e.g., by way of neural probes); a gain stage 300 coupled to receive FSA outputs; and a successive approximation register (SAR) ADC 400 coupled to receive gain stage outputs. The SAR ADC 400 is configured to provide digital outputs to the EC-PC neural processing architecture. Consequently, the FS neural recording architecture 500 can form portions of a multichannel analog front-end for the neural interface architecture 100.

Figure 5A:
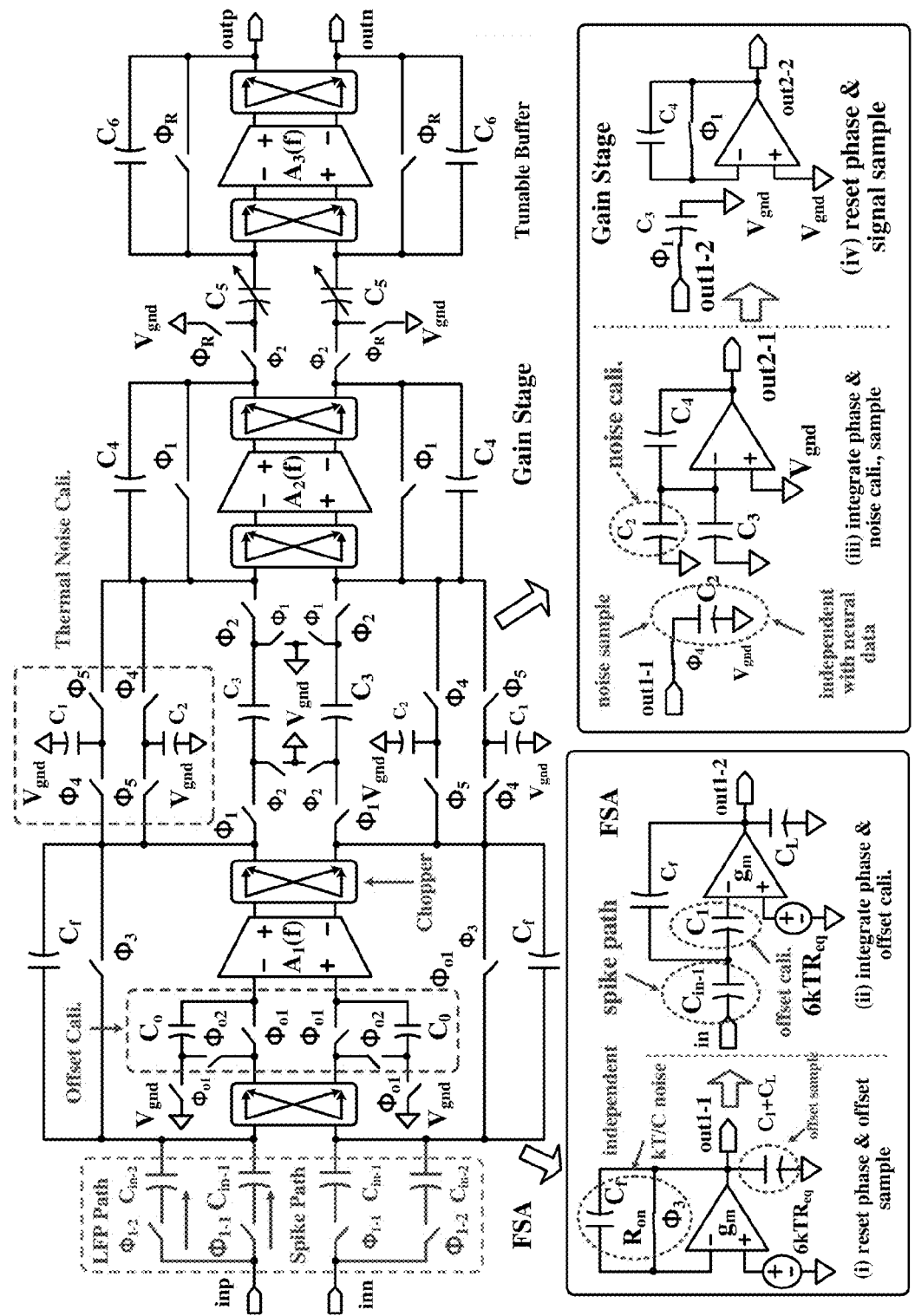
FIG. 5A is a schematic illustration showing portions of a representative embodiment of an FSA and a gain stage corresponding to the FS neural recording architecture of FIG. 4.
Figure 5B:
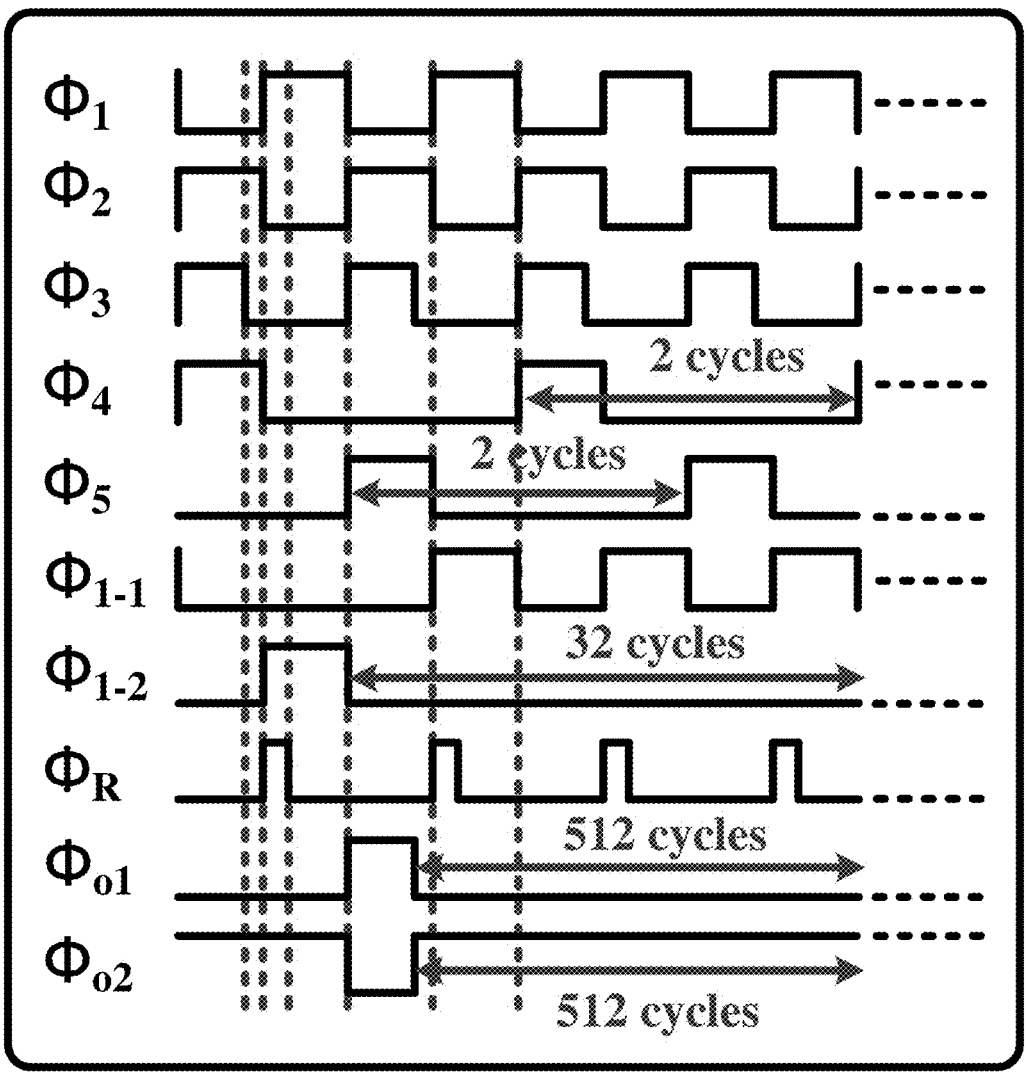
FIG. 5B provides a representative timing diagram corresponding to FIG. 5A.

FIG. 5A is a schematic illustration showing portions of a representative embodiment of an FSA 200 and a gain stage 300 corresponding to the FS neural recording architecture 500 of FIG. 4; and FIG. 5B provides a representative timing diagram corresponding to FIG. 5A.

Figure 6:
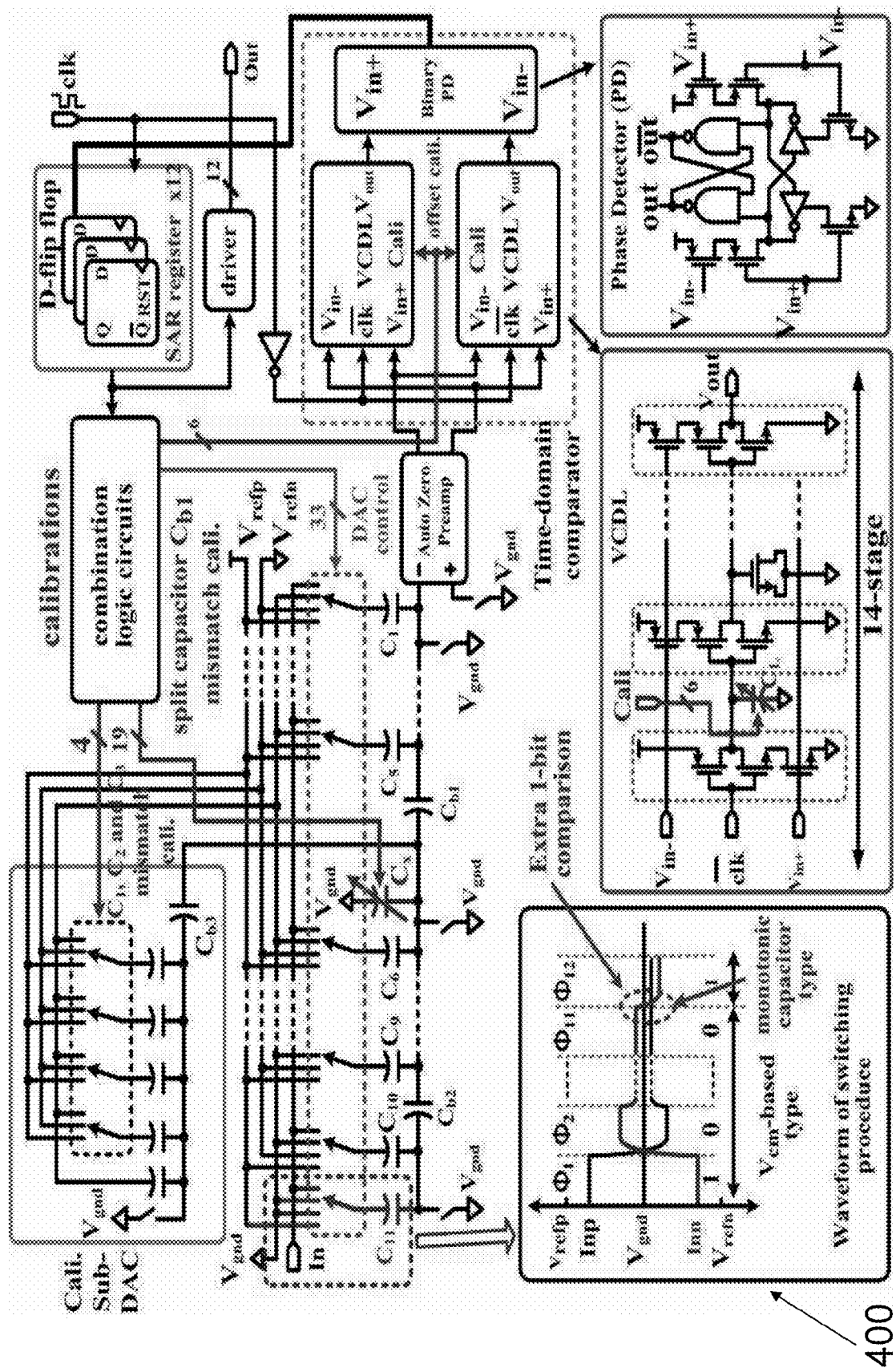
FIG. 6 is a schematic illustration of a representative successive approximation register (SAR) analog to digital converter (ADC) in accordance with an embodiment of the present disclosure.

FIG. 6 is a schematic illustration of a representative SAR ADC 600 in accordance with an embodiment of the present disclosure, which is configured to receive analog signals output provided by the gain stage 500, and generate digital signals corresponding thereto. The SAR ACD 600 is configured to have a wide dynamic range (DR).

Figure 7A:
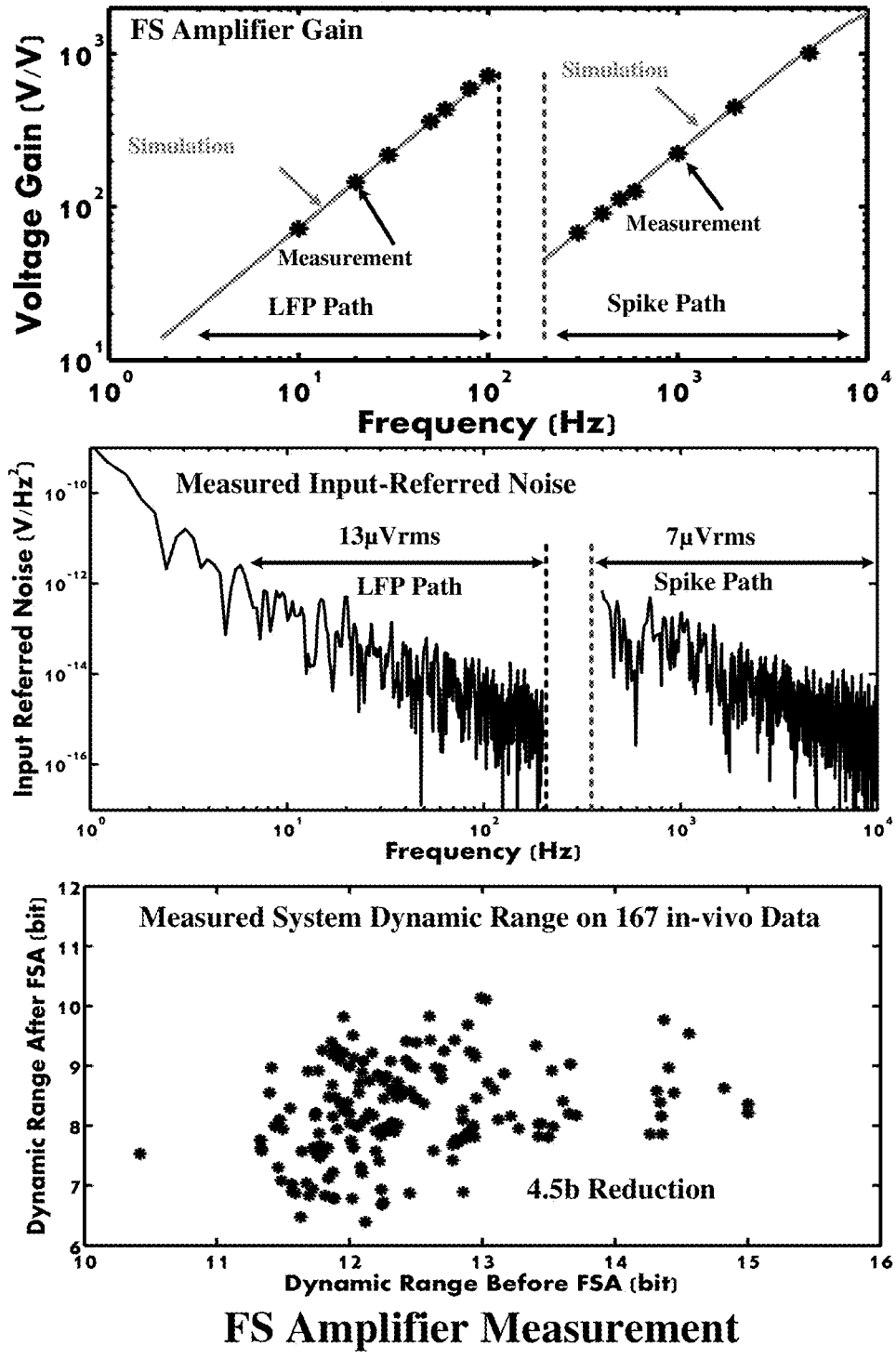
FIGS. 7A and 7B illustrate representative measurement results corresponding to the FSA and the SAR ADC of FIGS. 5A and 6.
Figure 7B:
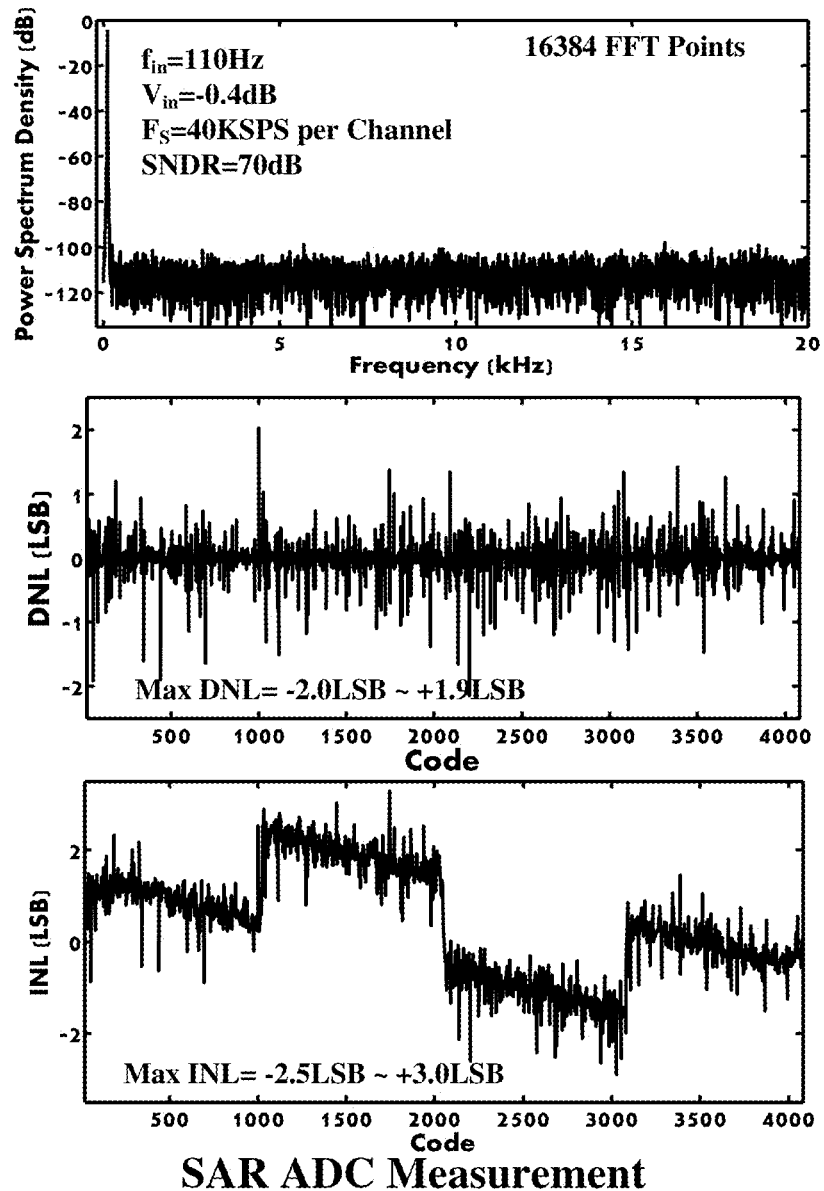
Figures 8A, 8B:
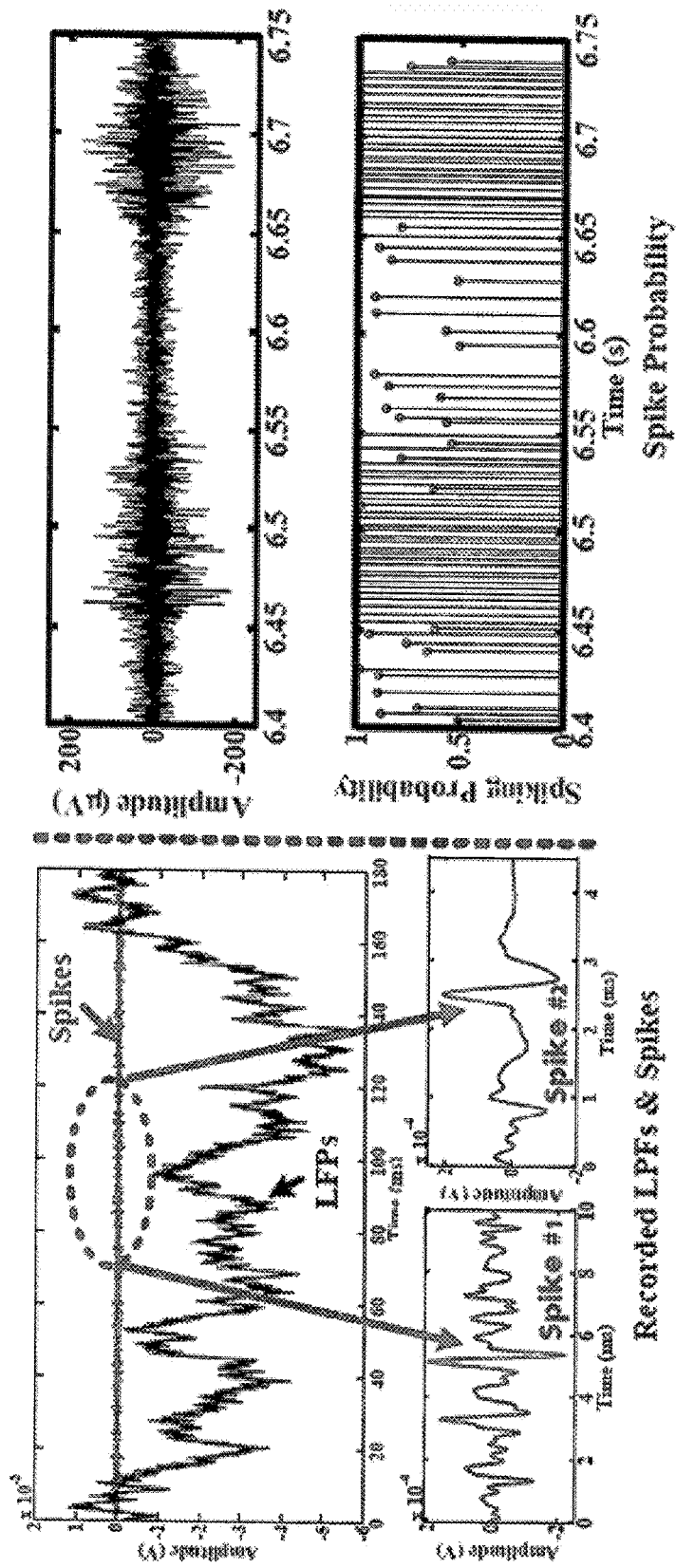
FIG. 8A illustrates local field potentials (LFPs) and extracellular spikes recorded by the FS neural recording architecture of FIG. 4 by way of a microwire array implanted in a rat hippocampus.
FIG. 8B illustrates a representative spike probability map generated by way of an EC-PC neural processing architecture from neural rat hippocampus neural signals recorded by way of the FS neural recording architecture of FIG. 4.

FIGS. 7A and 7B illustrate representative measurement results corresponding to the FSA 200 and the SAR ADC 400. FIG. 8A illustrates local field potentials (LFPs) and extra-cellular spikes recorded by the FS neural recording architecture 500 by way of a microwire array implanted in a rat hippocampus. Such extracellular spike signals can be processed by an EC-PC neural processing architecture 600, which can generate a correlated or corresponding spike probability map that can indicate or identify the presence or likely presence of neural spikes, for instance, in a manner illustrated in FIG. 8B.

Thus, in various embodiments, the outputs of an FS recording architecture 500 can be provided to an EC-PC neural processing architecture 600. The EC-PC neural processing architecture 600 can perform a neural signal processing sequence that implements or executes an EC-PC neural spike detection algorithm. In a number of embodiments, the EC-PC neural processing architecture 600 can process or analyze input signals (e.g., received from an FS recording architecture 500) in accordance with an EC-PC based neural spike detection algorithm, and output (e.g., simultaneously/concurrently) LFP data, extracellular spike data, and a neural spiking activity map.

Figure 9:
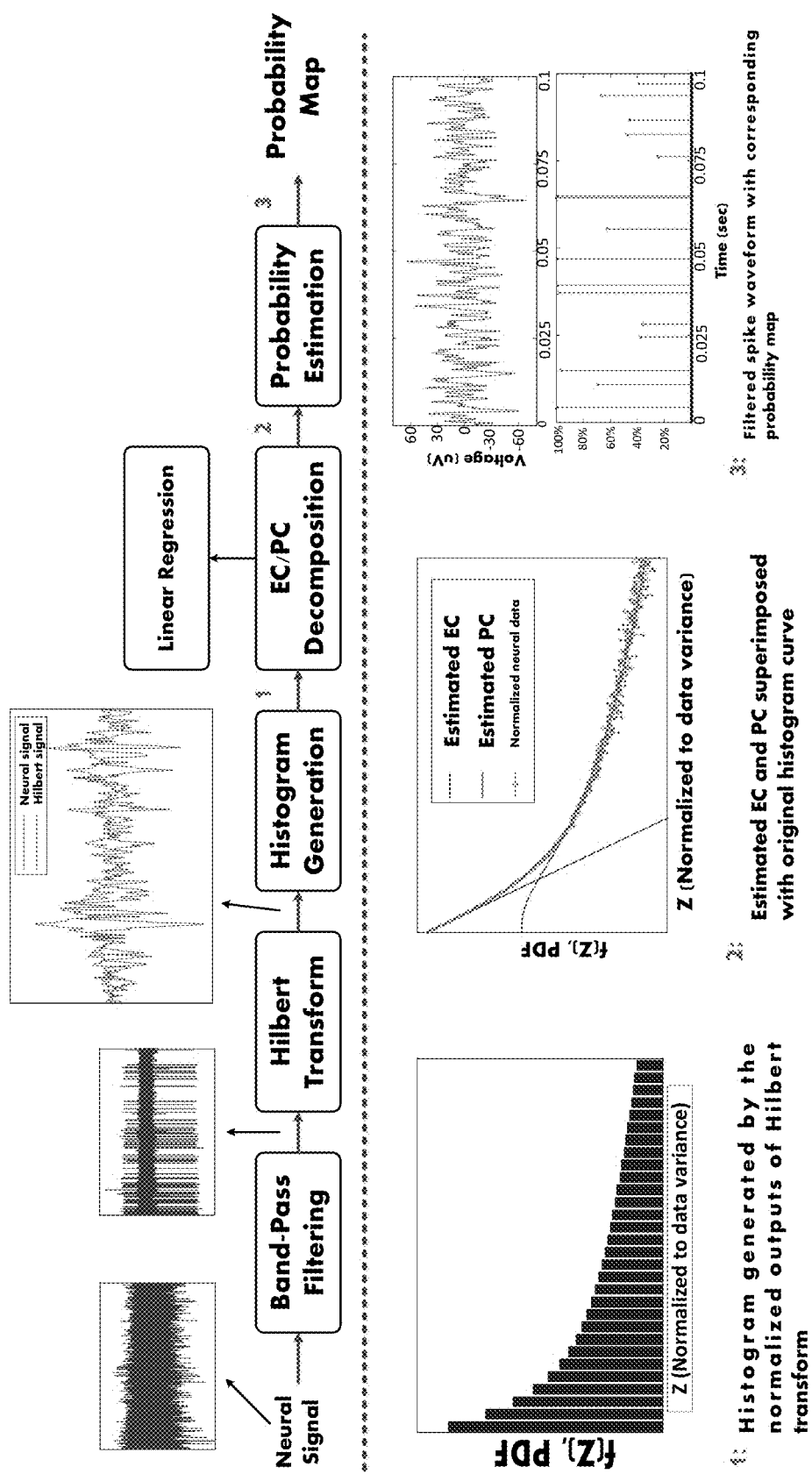
FIG. 9 depicts a neural signal processing sequence for EC-PC based neural spike detection in accordance with an embodiment of the present disclosure.

FIG. 9 depicts a neural signal processing sequence for EC-PC based neural spike detection in accordance with an embodiment of the present disclosure. Table 1 below provides an overview of an EC-PC neural spike detection algorithm correlated with or corresponding to the neural signal processing sequence of FIG. 9 in accordance with an embodiment of the present disclosure.

TABLE 1

EC-PC Based Neural Spike Detection Algorithm

Input: Digitized neural data $V(m\Delta T)$, m is the sampling index and $\Delta T$ is the sampling interval.
Output: Probability map $p_s(m\Delta T)$ to indicate spike presence. For example, $p_s(m\Delta T)=1$ means the sample has a 100% chance to be true spikes.
 Band-pass filter $V(m\Delta T)$ into $V_{bpf}(m\Delta T)$.
 Transform $V_{bpf}(m\Delta T)$ into Hilbert space as $HV(m\Delta T)$, and form analytic signal $V_{st}(m\Delta T) = V_{bpf}(M\Delta T) + iHV(m\Delta T)$.
 Estimate the probability density function $f(Z)$, where $Z = V_{st}^2$.
 Decompose $f(Z)$ into two components,
 $\tilde{f}_n(Z) = e^{-\lambda_1 Z}$ (EC) and $\tilde{f}_d(Z) = Z^{-\lambda_2}$ (PC).
 Calculated $p_s(m\Delta T) = \tilde{f}_d(Z(m\Delta T)) \cdot (\tilde{f}_d(Z(m\Delta T)) + \tilde{f}_n(Z(m\Delta T)))^{-1}$.

In view of the foregoing, neural signals (e.g., recorded or generated neural signals) can be decomposed or represented in Hilbert space as a combination of two components, namely, (a) an exponential noise component, EC; and (b) a polynomial spike component, PC. A spiking probability map can be estimated from EC and PC, and the presence of spikes or spiking behavior within a neural signal sequence can be detected or identified based upon the spiking probability map. Such neural spike detection is nonparametric and self-adaptive, and can reliably detect neural spikes under different recording conditions such as firing state transitions, amplitude/waveform fluctuations, and non-stationary noise. Architectures, systems, circuits, methods, and processes for neural spike detection in accordance with embodiments of the present disclosure reduce computational complexity, for instance, compared with other neural spike detection techniques, such as template matching or wavelet-based techniques.

Figure 10:
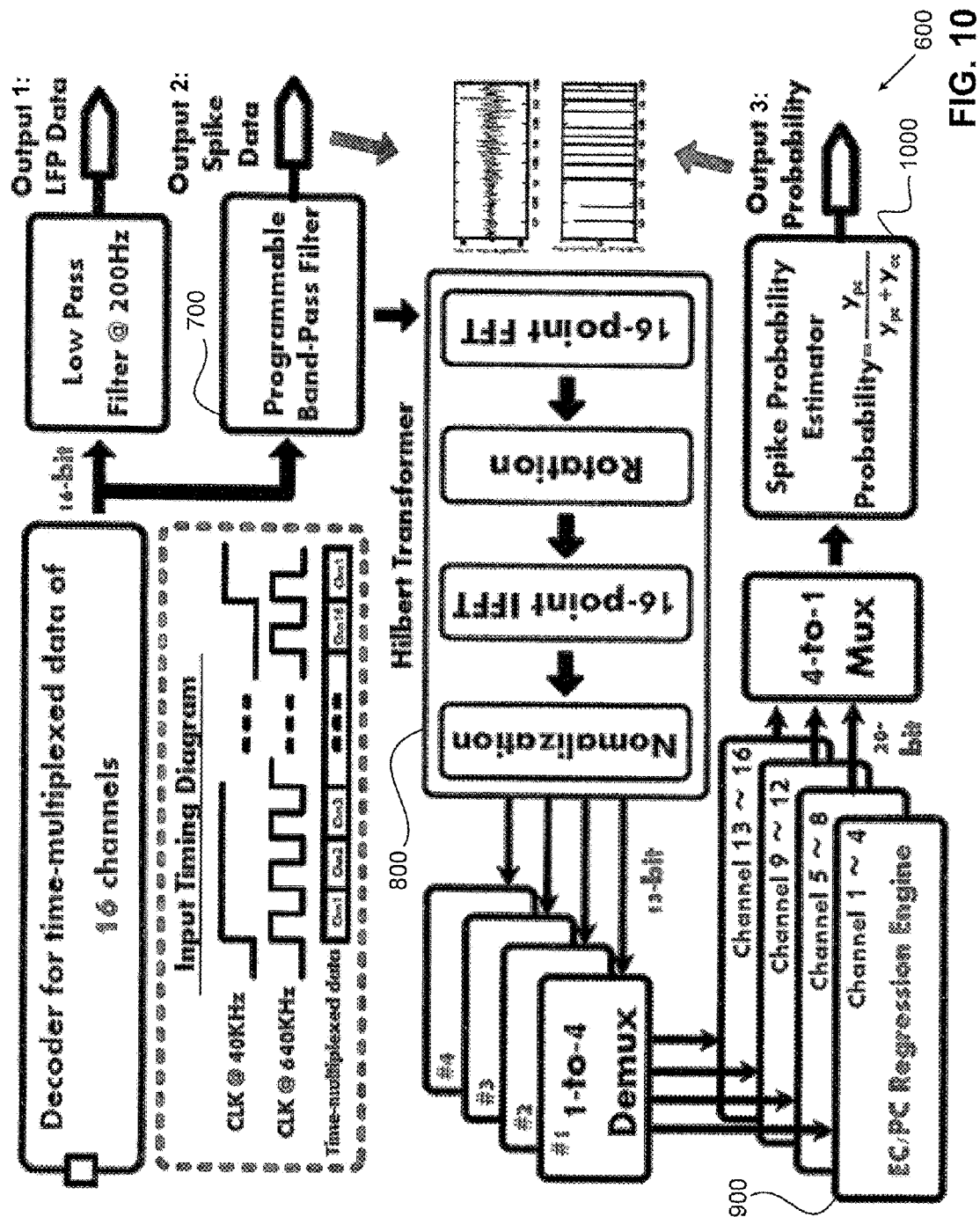
FIG. 10 is a schematic illustration of a representative EC-PC neural processing architecture in accordance with an embodiment of the present disclosure.

FIG. 10 is a schematic illustration of a representative EC-PC neural processing architecture 600 in accordance with an embodiment of the present disclosure, which can be implemented by way of at least one ASIC, FPGA, and/or other type of integrated circuit. In a representative implementation, the EC-PC neural processing architecture's inputs receive time-division multiplexed neural data over multiple (e.g., 16) channels.

Input neural data can be sampled and digitally represented in a predetermined manner, for instance, sampled at 40 kHz and represented by way of 32 bits, with 16 bits for data values and 16 bits for protocol information. The EC-PC neural processing architecture 600 can provide multiple types of output, including LFP data, spike data, and a spike probability map.

Figure 11:
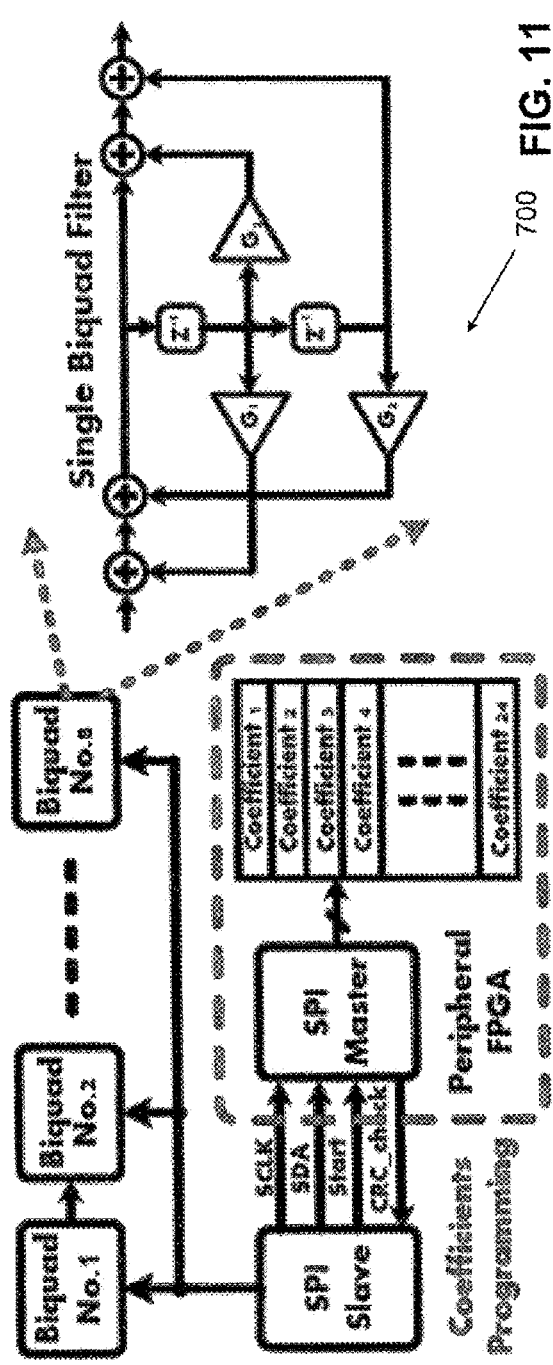
FIG. 11 is a schematic illustration of a programmable band-pass filter in accordance with an embodiment of the present disclosure.
Figure 12:
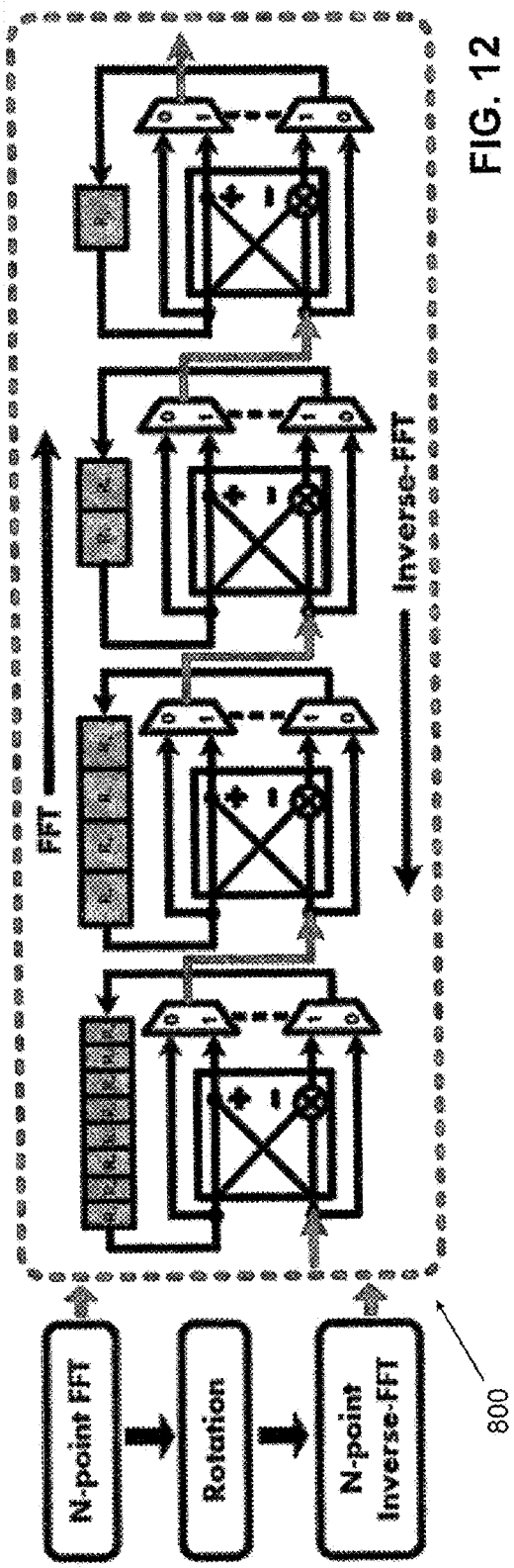
FIG. 12 is a schematic illustration of a Hilbert transformer in accordance with an embodiment of the present disclosure.
Figure 13:
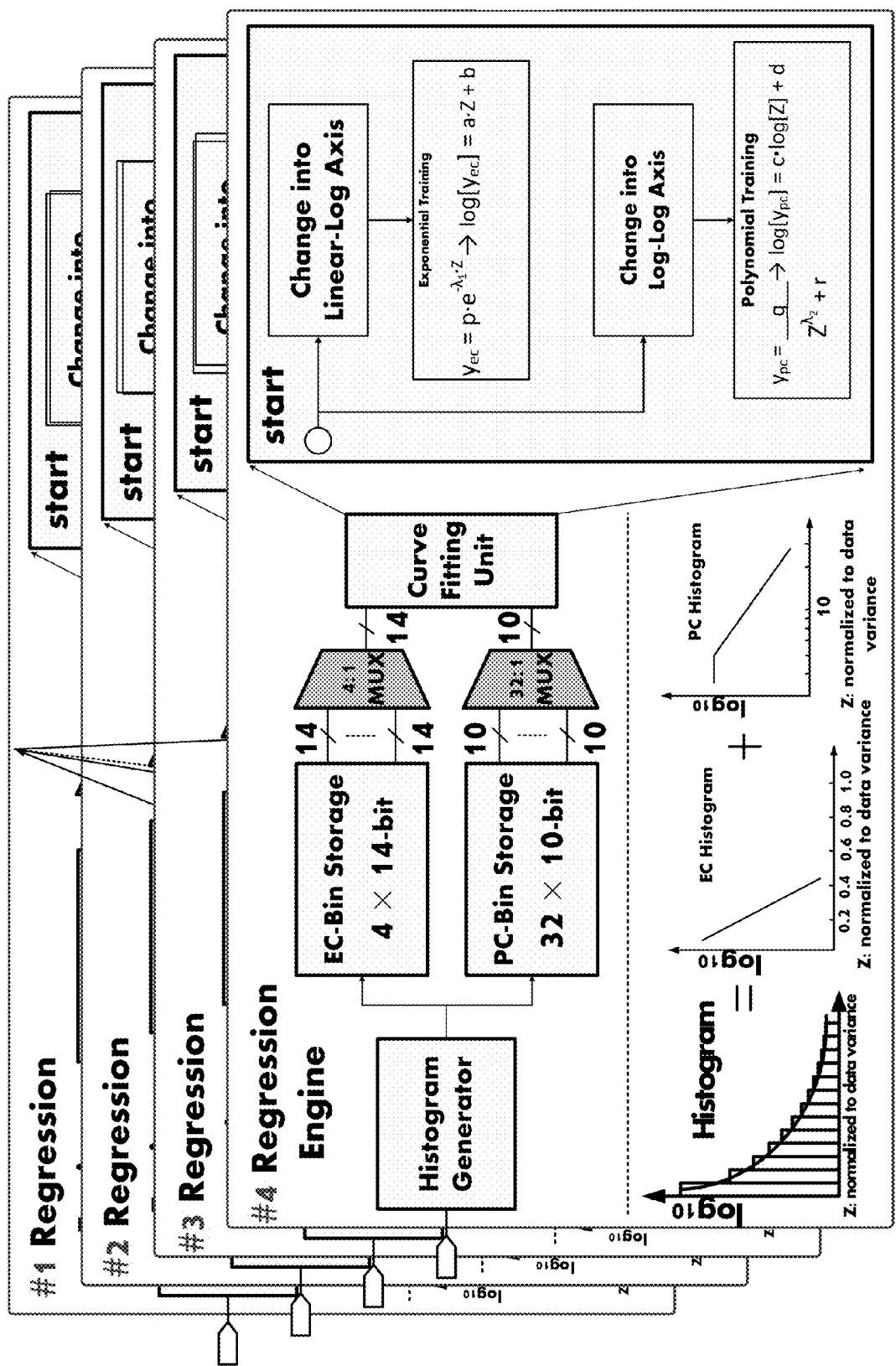
FIG. 13 is a schematic illustration of an EC-PC linear regression engine in accordance with an embodiment of the present disclosure.

In various embodiments, the EC-PC neural processing architecture 600 includes a programmable band-pass filter 700, an embodiment of which is further illustrated in FIG. 11; a Hilbert transformer 800, an embodiment of which is further illustrated in FIG. 12; a multichannel EC-PC linear regression engine 900, an embodiment of which is further illustrated in FIG. 13; and a neural spike probability estimator 1000.

With reference to FIG. 11, the programmable band-pass filter 700 provides a set of filters, such as infinite impulse response (IIR) filters, with tunable corner frequencies (e.g., with 300 Hz and 8 kHz as default corner frequencies), for instance, by way of multiple digital biquad filters cascaded in series. Programmability is supported by a serial peripheral interface (CPI). Cyclic redundancy check (CRC) can be incorporated to enhance data transmission reliability. Coefficient downloading through the SPI, and simultaneous CRC can be coordinated by an on-chip finite state machine (FSM).

The Hilbert transformer 800 of FIG. 12 converts bandpass filtered data to analytic form by performing Hilbert transforms upon such data. One having ordinary skill in the relevant art will understand that extracellular spikes can exhibit significant variations in shape, and would conventionally require multiple detection windows. By performing a Hilbert transform upon neural signal data, embodiments in accordance with the present disclosure require only one detection window. Furthermore, neural data has a compact representation in Hilbert space, which simplifies EC-PC decomposition. The Hilbert transformer 800 can be based upon a Fast Fourier Transform (FFT)—inverse FFT engine, for instance, a Radix-2 single delay feedback (R2SDF) architecture configured for performing FFT—inverse FFT operations.

With reference to FIG. 13, the EC-PC linear regression engine 900 estimates EC and PC coefficients or parameters, and calculates neural spike probability maps based upon the EC and PC coefficients/parameters. In an embodiment, the EC-PC linear regression engine 900 includes a histogram generator; an EC parameter accumulator, bin, or storage unit; a PC parameter accumulator, bin, or storage unit; and a curve fitting unit. For a 16 channel implementation, to ensure adequate training accuracy, the word length of histogram bins for EC and PC estimation can be 14 bits and 10 bits, respectively. A single histogram can be sequentially shared by multiple (e.g., 4) channels in order to reduce histogram data storage requirements (e.g., by a corresponding factor of 4). Simulation results indicate that a 2.5 second training period for switching histograms among channels can give rise to reliable estimation of neuron firing rates, patterns, or behavior. By setting the training period to be 2.5 seconds, each channel's coefficients are updated every 10 seconds (based upon the 2.5 seconds of training).

The EC and PC parameter bins are time-multiplexed, and their bin outputs are processed by the curve fitting units, which simultaneously perform two first order linear regression tasks in linear-log and log-log axes, respectively. After each time multiplexed period, one regression engine is switched to a next channel, and this regression engine builds another histogram. Switching is scheduled by a control unit configured for coordinating the operation of each regression engine. At the end of each training period, EC and PC curve fitting units are activated, which estimate EC and PC coefficients, respectively, within a short time interval (e.g., 0.75 milliseconds). The estimated EC and PC coefficients of a given channel can remain constant until the regression engine for that channel is subsequently switched back or cycled again to that channel.

The neural spike probability estimator 1000 receives the outputs generated by the EC-PC linear regression engine 900, and generates or outputs a corresponding neural spike or spiking probability map. The existence, occurrence, or likely occurrence of individual neural spikes can be determined by applying a threshold condition to data within the spike probability map.

Aspects of Data Rate Reduction

When considering the acquisition and processing of neural signals generated by a significant or large number of neurons, such as a quantity or population of neurons that is expected to be relevant to initiating, controlling, and/or performing one or more types of biological activity, the raw data rate and real-time neural signal processing requirements become quite computationally intensive. For instance, for one million neurons, the raw data rate can be or reach approximately 1 Terabits per second (Tbps). Ideally, the detection of neural spiking activity from neural signals acquired or provided at this data rate should occur in real, essentially real, or near-real time. At such a data rate, recording raw neural spiking signals, communicating such signals to a remote system or device for processing, and analyzing the neural spiking signals in real time to identify the existence of neural spikes is generally not feasible.

Figure 14:
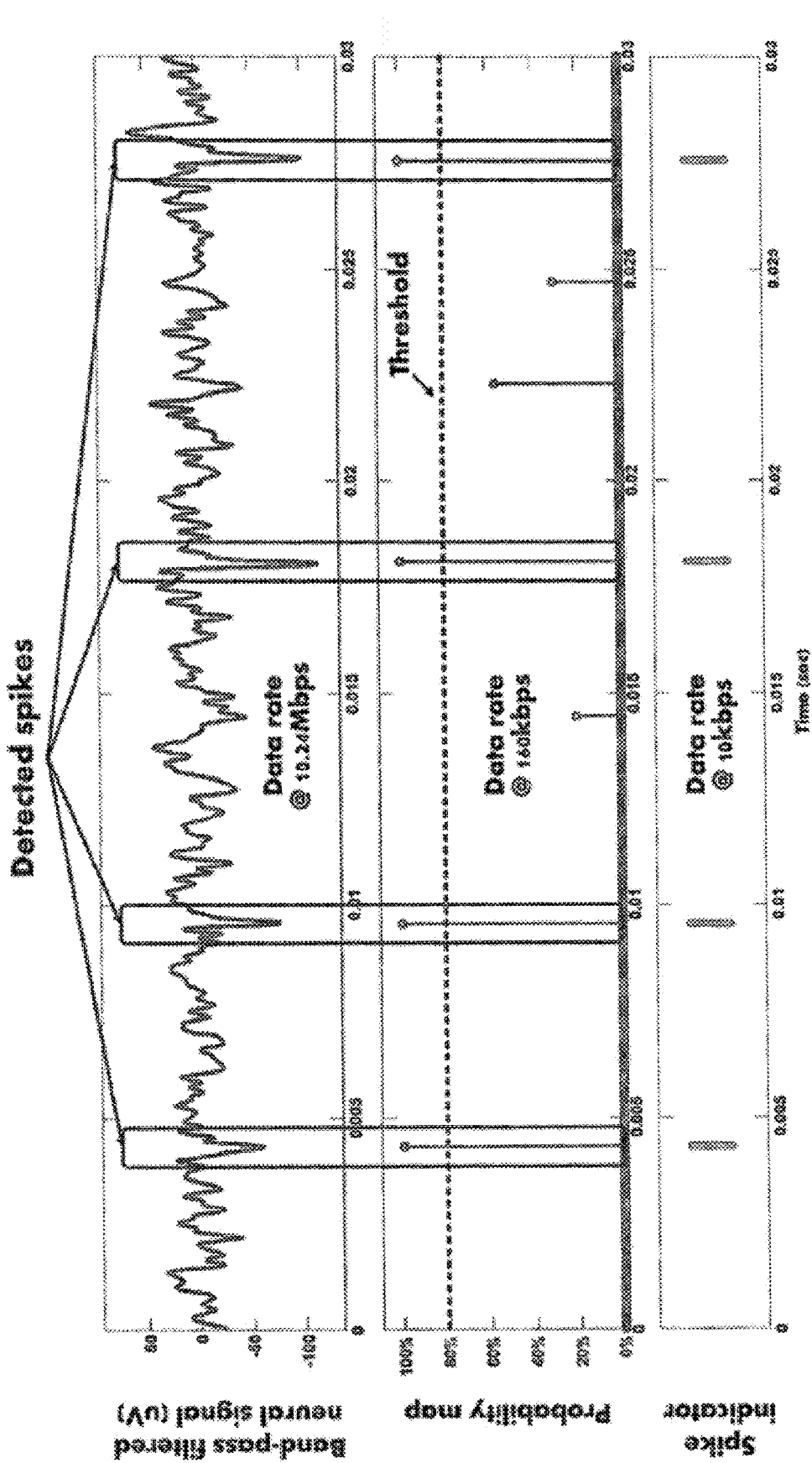
FIG. 14 illustrates a representative data rate reduction providable by an EC-PC neural processing architecture in accordance with an embodiment of the present disclosure.

An EC-PC neural processing architecture 600 in accordance with an embodiment of the present disclosure can greatly or dramatically reduce the data rate associated with identifying and/or communicating the likely presence or existence of neural spikes to one or more other systems. FIG. 14 illustrates a representative data rate reduction providable or attainable by an EC-PC neural processing architecture 600 in accordance with an embodiment of the present disclosure. For a representative 16 channel EC-PC neural processing architecture 600, a sampling frequency of each channel can be 40 kHz, and individual neural signal data values can be quantized as 16 bits, which contributes to a net raw data rate for bandpass filtered neural spike data of 10.24 Mbps. A data rate corresponding to the generation of spike probability maps is 160 kbps, and a data rate corresponding to the generation of neural spike indicators under an 80% threshold condition and "winner take all" strategy imposed upon the spike probability maps is 10 kbps. Thus, an EC-PC neural processing architecture 600 in accordance with an embodiment of the present disclosure can provide a data rate reduction for the generation of spike probability maps that is more than an order of magnitude (e.g., 50, 60, or more times) less than the raw neural spike data rate; and a further data rate reduction for the generation of neural spike indicators that is approximately three orders of magnitude (e.g., 1000 times) less than the raw neural spike data rate.

An EC-PC neural processing architecture 600 in accordance with an embodiment of the present disclosure can be scaled to process captured/recorded or generated neural spike data corresponding to one million or more neurons in real time, and output neural spike indicators at reasonable or technologically feasible data rates. A neural interface architecture 100 in accordance with an embodiment of the present disclosure can be coupled to or form a portion of a brain computer interface (BCI) that is configured for analyzing neural activity of small, moderate, or substantial numbers of neurons, and possibly performing one or more actions (e.g., controlling automated or semi-automated equipment, devices, or processes, for instance, by way of a closed-loop system) based upon neural activity.

While certain embodiments described herein are directed to integrated circuit implementations of neural signal interfaces and neural signal processing architectures, an individual having ordinary skill in the relevant art will understand that in other embodiments, one or more aspects relating to receiving, processing, or analyzing neural signals can occur by way of a computer-based system having a processing unit configured for executing stored program instructions, and a memory in which program instructions reside directed to processing neural signals in accordance with a neural signal spiking model that includes an exponential component and a polynomial component as described herein. Such program instructions can additionally or alternatively be stored on one or more computer-readable media (e.g., hard disk drives, or removable storage media such as optical media, etc. . . . ).

Aspects of particular embodiments in accordance with the present disclosure address at least one aspect, problem, limitation, and/or disadvantage associated with exiting architectures, systems, apparatuses, devices, and procedures for neural signal interfacing and/or processing. While features, aspects, and/or advantages associated with certain embodiments have been described in the disclosure, other embodiments may also exhibit such features, aspects, and/or advantages, and not all embodiments need necessarily exhibit such features, aspects, and/or advantages to fall within the scope of the disclosure. It will be appreciated by a person of ordinary skill in the art that several of the above-disclosed systems, components, processes, or alternatives thereof, may be desirably combined into other different systems, components, processes, and/or applications. In addition, various modifications, alterations, and/or improvements may be made to various embodiments that are disclosed by a person of ordinary skill in the art within the scope of the present disclosure.

The invention claimed is:

1. A method for processing signals comprising:
processing a signal sequence into a probability density function f(Z) for each of a plurality of channels by a processing unit;
decomposing the probability density function f(Z) into an exponential component (EC) and a power-law component (PC) for each of the plurality of channels using at least one multi-channel EC-PC linear regression engine;
sequentially and cyclically allocating the regression engine to each of the plurality of channels to successively build a plurality of histograms, wherein allocation of the regression engine to each of the plurality of channels lasts for a training period; and
for a given channel of the plurality of channels, cyclically outputting updated estimated EC and PC coefficients for the given channel at a rate given by the training period multiplied by the number of channels within the plurality of channels,
wherein the exponential component is correlated with the presence of noise within the signal sequence and the power-law component is correlated with the presence of detectable spikes within the signal sequence distinguishable from the noise.

2. The method of claim 1, wherein providing the signal sequence comprises one of providing neural signals produced by physical neurons and providing simulated neural signals.

3. The method of claim 1, wherein the exponential component corresponds to background noise within the signal sequence that satisfies the Central Limit Theorem.

4. The method of claim 3, wherein the power-law component corresponds to the occurrence of spikes within the signal sequence that violate Lyapunov's condition.

5. The method of claim 4, wherein the magnitude of the power-law component relative to the magnitude of the exponential component increases in response to each of increased spike magnitude and increased spike occurrence frequency within the signal sequence.

6. The method of claim 1, wherein the exponential component mathematically corresponds to an equation of the form $$e^{-\lambda_1 Z}$$

and the power-law component mathematically corresponds to an equation of the form $$Z^{-\lambda_2}.$$

7. The method of claim 6, wherein $\lambda_1$ approximately equals 0.5, and $\lambda_2$ approximately equals 2.5.

8. The method of claim 6, wherein the presence of signal values within the signal sequence corresponding to noise gives rise to f(Z) behaving in accordance with the exponential component and the presence of signal values within the signal sequence corresponding to neural spikes gives rise to f(Z) behaving in accordance with the power-law component.

9. The method of claim 8, wherein processing the signal sequence further comprises determining a spike detection threshold corresponding to a mathematical crossover point between the exponential component and the power-law component.

10. The method of claim 1, further comprising determining a probability that a signal value within the signal sequence corresponds to one of noise and a spike based on the exponential component and the power-law component.

11. The method of claim 10, further comprising generating a spiking probability map corresponding to the signal sequence, the spiking probability map indicating which signal values within the signal sequence correspond to neural spikes.

12. The method of claim 11, further comprising outputting a sequence of spike indicators based upon the spiking probability map, wherein a data rate corresponding to the sequence of spike indicators is approximately 1000 times less than a raw data rate corresponding to recorded neural signals.

13. The method of claim 1, wherein processing the signal sequence comprises performing a Hilbert transform upon the signal sequence.

14. An integrated circuit for processing signals, comprising:
a processing unit configured for processing a signal sequence into a probability density function f(Z) for each of a plurality of channels;
at least one multi-channel EC-PC linear regression engine configured for decomposing the probability density function f(Z) into an exponential component (EC) and a power-law component (PC) for each of the plurality of channels,
wherein the exponential component is correlated with the presence of noise within the signal sequence and the power-law component is correlated with the presence of detectable spikes within the signal sequence distinguishable from the noise,
wherein the regression engine is sequentially and cyclically allocated to each of the plurality of channels to successively build a plurality of histograms, wherein allocation of the regression engine to each of the plurality of channels lasts for a training period,
wherein for a given channel of the plurality of channels, updated estimated EC and PC coefficients for the given channel is cyclically output at a rate given by the training period multiplied by the number of channels within the plurality of channels.

15. The method of claim 1, wherein the method is implemented on a single integrated circuit to detect and identify individual neural spikes within the signal sequence for each of the plurality of channels.

16. The method of claim 1, further comprising:
receiving input signals corresponding to neuroelectric activity using a frequency shaping amplifier (FSA); and
receiving and amplifying signals output by the FSA using an amplifier gain stage.

17. The method of claim 16, wherein an electrode offset voltage $V_{off}$ is inherently rejected by way of the FSA, and wherein the method excludes filtering electrical signals that are input to a neural interface and which correspond to neuroelectric activity using a DC high pass filter.

18. The integrated circuit of claim 14, wherein the at least one multi-channel EC-PC linear regression engine comprises a plurality of multi-channel EC-PC linear regression engines, and wherein each of the plurality of multi-channel EC-PC linear regression engines is configured to receive a subset of the plurality of channels, and wherein each of the plurality of multi-channel EC-PC linear regression engines is time-multiplexed.

19. The integrated circuit of claim 14, further comprises:
a neural spike probability estimator configured for generating a neural spike probability map based upon the exponential component and the power-law component for each of the plurality of channels.

20. The integrated circuit of claim 19, further comprising a neural interface, the neural interface comprising:
a frequency shaping amplifier (FSA) configured for receiving input signals corresponding to neuroelectric activity; and
an amplifier gain stage coupled to the FSA and the at least one multi-channel EC-PC linear regression engine to receive and amplify signals output by the FSA for providing the signal sequence comprising a plurality of signal values.

21. The integrated circuit of claim 20, wherein the neural interface inherently rejects electrode offset voltage $V_{off}$ by way of the FSA, and wherein the neural interface excludes a DC high pass filter configured for filtering electrical signals that are input to the neural interface and which correspond to neuroelectric activity.

22. The integrated circuit of claim 20, wherein the neural interface further comprises an analog-to-digital conversion (ADC) stage coupled to the amplifier gain stage, the ADC stage configured for converting amplified FSA output signals to digital signals.

23. The integrated circuit of claim 22, wherein the processing unit comprises a Hilbert transformer coupled to the ADC stage, the Hilbert transformer configured for performing a Hilbert transform upon neural signal data received from the ADC stage.

24. The integrated circuit of claim 23, wherein the at least one multi-channel EC-PC linear regression engine is coupled to the Hilbert transformer, the at least one multi-channel EC-PC linear regression engine configured for estimating the EC and PC coefficients corresponding to Hilbert transformed neural signal data.

* * * * *